US009340495B2

(12) United States Patent
Hashmi et al.

(10) Patent No.: US 9,340,495 B2
(45) Date of Patent: May 17, 2016

(54) PROCESS FOR THE PREPARATION OF ISOBUTYLIDENE DIUREA

(71) Applicant: SAUDI BASIC INDUSTRIES CORPORATION, Riyadh (SA)

(72) Inventors: Syed Azhar Hashmi, Riyadh (SA); Abdullah Bin-Nafisa, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/415,039

(22) PCT Filed: Jul. 18, 2013

(86) PCT No.: PCT/IB2013/055928
§ 371 (c)(1),
(2) Date: Jan. 15, 2015

(87) PCT Pub. No.: WO2014/016745
PCT Pub. Date: Jan. 30, 2014

(65) Prior Publication Data
US 2015/0183729 A1 Jul. 2, 2015

(30) Foreign Application Priority Data
Jul. 23, 2012 (EP) .................................... 12005353

(51) Int. Cl.
*C07C 273/18* (2006.01)
*C05C 9/00* (2006.01)
*C07C 275/14* (2006.01)

(52) U.S. Cl.
CPC ............ *C07C 273/1863* (2013.01); *C05C 9/00* (2013.01); *C07C 275/14* (2013.01); *Y10T 428/2982* (2015.01)

(58) Field of Classification Search
CPC .. C07C 273/1863; C07C 275/14; C05C 9/00; Y10T 428/2982
See application file for complete search history.

(56) References Cited

U.S. PATENT DOCUMENTS

| 3,322,528 | A |  | 5/1967 | Hamamoto et al. |
| 3,326,665 | A |  | 6/1967 | Schafer et al. |
| 3,441,539 | A |  | 4/1969 | Schafer et al. |
| 3,870,755 | A |  | 3/1975 | Kamo et al. |
| 3,962,329 | A |  | 6/1976 | Schoenaich et al. |
| 4,062,890 | A |  | 12/1977 | Shank |
| 5,124,451 | A | * | 6/1992 | Hackl ............... C07C 273/1854 544/169 |
| 5,169,954 | A | * | 12/1992 | Hackl ................ C07D 295/215 544/169 |
| 5,414,083 | A | * | 5/1995 | Hackl ................ C07D 295/215 544/130 |
| 5,597,917 | A | * | 1/1997 | Hackl ................ C07D 295/215 544/130 |

FOREIGN PATENT DOCUMENTS

| DE | 1146080 |  | 3/1963 |
| DE | 1905834 | A1 | 9/1970 |
| DE | 142044 |  | 6/1980 |
| DE | 4128828 | A1 | 3/1993 |
| DE | 19631764 | A1 | 2/1998 |
| EP | 0877722 |  | 11/1998 |
| GB | 1212605 |  | 11/1970 |

OTHER PUBLICATIONS

Reddy "New environmentally friendly solvent free synthesis of dihydropyrimidinones catalysed by N-butyl, N,N-dimethyl-a-phenylethylammonium bromide" Tetrahedron Letters, 2003, 44, 8173-8175.*
Mobinikhaledi "Synthesis of Some 2-Oxo and 2-Thioxo Substituted Pyrimidine Using Solvent-free Conditions" Journal of Heterocyclic Chemistry, 44, 697-699, 2007.*
Bose "New protocol for Biginelli reaction—a practical synthesis of Monastrol" ARKIVOC 2005 (iii) 228-236.*
European Search Report for Application No. 12005353.3; Date of Search: Nov. 19, 2012; Date of Mailing Nov. 28, 2012; 7 Pages.
International Search Report for International Publication No. PCT/IB2013/055928; International Filing Date: Jul. 18, 2013; Date of Mailing Oct. 28, 2013; 5 Pages.
Machine Translation of DD142044(A1); Jun. 4, 1980; 21 Pages.
Machine Translation of DE1146080(B); Mar. 28, 1963; 35 Pages.
Ullmann's Encyclopedia of Industrial Chemistry; 5th Edition; vol. 10: "Ethanolamines and Propanolamines to Fiber, 4 Synthetic Organic;" Dec. 28, 1987; pp. 363-401.
Written Opinion of the International Searching Authority for International Publication No. PCT/IB2013/055928; International Filing Date: Jul. 18, 2013; Date of Mailing Oct. 28, 2013; 6 Pages.

\* cited by examiner

*Primary Examiner* — Jafar Parsa
*Assistant Examiner* — Amy C Bonaparte
(74) *Attorney, Agent, or Firm* — Cantor Colburn LLP

(57) ABSTRACT

The invention relates to a process comprising: reacting isobutyraldehyde with an aqueous solution of urea in the presence of a phase transfer catalyst to form isobutylidene diurea. Preferably, the phase transfer catalyst is a quaternary ammonium salt, more preferably benzyltriethylammonium chloride. Even more preferably, the process is performed in one pot.

9 Claims, No Drawings

PROCESS FOR THE PREPARATION OF ISOBUTYLIDENE DIUREA

CROSS REFERENCE TO RELATED APPLICATIONS

This application is a 371 of International Application No. PCT/IB2013/055928, filed Jul. 18, 2013, which claims priority to European Application No. 12005353.3, filed Jul. 23, 2012, both of which are hereby incorporated by reference in its entirety.

The invention relates to a process for the preparation of isobutylidene-diurea, to isobutylidene-diurea obtainable by said process and to the use of said isobutylidene-diurea as a fertilizer.

Isobutylidene-diurea (IBDU) is a condensation product of urea and isobutyraldehyde. IBDU is used as a slow acting nitrogeneous fertilizer and may be used—instead of urea—as a source of nitrogen in the nutrition of ruminants.

Processes for the preparation of IBDU are known in the art.

For example, many processes for the preparation of IBDU involve reaction of urea with isobutyraldehyde in an aqueous, acidic solution with vigorous mixing (see for example U.S. Pat. No. 3,322,528; U.S. Pat. No. 3,326,665; U.S. Pat. No. 3,441,539, GB949,408; GB1,099,643; or GB 1,212,605). A primary drawback of these techniques for manufacturing IBDU however, is the relative lack of control over the condensation reaction. That is, the reaction rate and total time of reaction are most difficult to control. Often, such condensation reactions proceed at a rather slow and unpredictable pace, frequently requiring a 10 to 30 minute reaction time. There is, therefore, a continuing need in the art for improved techniques for manufacturing IBDU.

For example, U.S. Pat. No. 3,962,329 discloses a continuous process for the production of solid granular isobutylidene diurea by condensation of urea with isobutyraldehyde in the presence of a mineral acid as a catalyst, wherein phosphoric and sulphuric acid are added alternately at different intervals of time to the continuous feed of the urea and isobutyraldehyde. The presence of a mineral or other acid for conducting the condensation of urea with isobutyraldehyde to form IBDU is also taught by DE1543201, DE1146080, and U.S. Pat. No. 3,870,755.

However, the use of a (strongly) corrosive (mineral) acid as a catalyst for this reaction requires the use of special metallurgy and handling techniques. Furthermore, work-up of the IBDU produced in said processes is difficult as it requires for example the use of lots of base to neutralize the final product.

For example, U.S. Pat. No. 4,062,890 describes a process for manufacturing IBDU comprising reacting urea with isobutylaldehyde in an aqueous medium in the presence of an protein derived emulsifier and an inorganic ammonium salt at an alkaline pH.

It is further described that 'A preferred mode of carrying out this reaction involves mixing the desired amounts of urea, collagen-derived emulsifier and inorganic ammonium salt with water, and heating this aqueous phase to a temperature in excess of about 40° C. Thereafter, addition of the desired amount of isobutyraldehyde to the aqueous reaction medium, along with vigorous agitation, results in emulsification of the system and an immediate condensation reaction between the urea and isobutyraldehyde. Usually, the exothermic condensation reaction will increase the reaction temperature to from about 65° C. to 100° C. Due to the presence of the urea and inorganic ammonium salt, and the absence of any acidic catalysts, the reaction proceeds at a pH of from about 7.0 to 9.0. Within the first 2-3 minutes of reaction, the reaction mass progresses from a creamy texture to a soft solid. At this time, the reaction mass should be removed from the reaction vessel, and the exothermic condensation reaction is allowed to proceed until completed.'

However, this process requires protein-derived emulsifier in large quantities, which is not industrially feasible. Also, the inorganic ammonium salt cannot be (easily) removed from the IBDU produced. Moreover, the reaction temperature increase to 100° C. may result in evaporation of isobutyraldehyde and hence a lower yield.

Therefore it is an object of the invention to provide an improved process for the preparation of isobutylidene diurea.

This object is achieved by a process comprising the step of reacting isobutyraldehyde with an aqueous solution of urea in the presence of a phase transfer catalyst to form isobutylidene diurea.

The process of the invention provides an easy process for the preparation of isobutylidene diurea, which can be conducted at a low temperature. The process may additionally have a short reaction time and/or a high yield (e.g. in the range from 90 to 100%).

The process is easy, since it does not require corrosive mineral acids, a protein emulsifier and there is no need to control the pH of the reaction. Furthermore, since the reaction in the process of the invention can be performed at low temperature and is mildly exothermic, there is no need for strong cooling or control of the reaction temperature.

Furthermore, the formed IBDU is relatively easily purified and the phase transfer catalyst may be recycled.

Isobutyraldehyde may be used in its pure form, or may be present in a suitable solvent. Examples of suitable solvents include but are not limited to solvents that do not significantly interfere with the condensation of isobutyraldehyde with urea and are not prohibited for the use of the formed IBDU as a fertilizer or in feed. Examples of such solvents include but are not limited to organic solvents, for example ethanol. Preferably, for a high reaction rate, isobutyraldehyde is used in concentration of at least 95 wt %, more preferably the isobutyraldehyde used is (substantially) pure.

The aqueous solution of urea may for example contain urea in an amount from 20 to 90 wt %. Preferably, the aqueous solution of the urea contains the urea in an amount from 40 to 85 wt %, for example from 50 to 80 wt % or from 50 to 85 wt %.

Any suitable phase transfer catalyst may be used in the process of the present invention. Examples of suitable phase transfer catalysts include but are not limited to quaternary ammonium salts, for example benzyltriethylammonium chloride or tetrabutyl ammonium sulphate or bis-quaternary ammonium salts, for example the commercially available Triburon chloride (6-[dimethyl-[1-methyl-3-(2,2,6-trimethylcyclohexyl)propyl]ammonio]hexyl-dimethyl-[1-methyl-3-(2,2,6-trimethylcyclohexyl)propyl]ammonium dichloride). Preferably, the phase transfer catalyst is benzyltriethylammonium chloride Preferably, in the process of the invention, the step of reacting isobutyraldehyde with an aqueous solution of urea in the presence of a phase transfer catalyst to form isobutylidene diurea is performed in one pot. This makes the process of the invention very economical as compared to the known processes.

The temperature at which the reaction of isobutyraldehyde with urea is carried out is preferably below the boiling point of isobutyraldehyde and water and is preferably below 100° C., more preferably at most 80° C., more preferably at most 60° C., for example at most 50° C. and/or at least 20° C., for example at least 30° C. Preferably, the temperature at which the reaction of isobutyraldehyde with urea is carried out is in the range from 20 to 50° C.

Preferably, the pressure for the reaction of isobutyraldehyde with urea is atmospheric pressure (around 0.1 MPa).

The reaction of isobutyraldehyde with an aqueous solution of urea is preferably performed without a further solvent.

The molar ratio of isobutyraldehyde to urea is in principle not critical, but is preferably chosen close to the stochiometric ratio. For example, the molar ratio of isobutyraldehyde to urea is preferably chosen from 1:1 to 1:3, more preferably around 1:2.

The phase transfer catalyst need only be present in the process of the invention in catalytic amounts. For example, the molar amount of phase transfer catalyst, for example benzyltriethylammonium chloride, to one mole of isobutyraldehyde, may be in the range from 0.005 to 0.05, for example from 0.01 to 0.05 and is preferably from 0.02 to 0.04, more preferably about 0.03 mol. In other words, the amount of phase transfer catalyst, preferably benzyltriethylammonium chloride is preferably in the range from 0.5 to 5 mol %, for example from 1 to 5 mol % of the isobutyraldehyde and is preferably from 2 to 4 mol %, more preferably about 3 mol % of the isobutyraldehyde.

The process of the invention may further comprise the step of isolating the isobutyilidene diurea to obtain isolated isobutylidene diurea. Suitable isolation techniques are known to the skilled person and examples of such techniques include but are not limited to filtration and centrifugation.

The process of the invention may further comprise the step of mixing the formed isobutylidene diurea or the isolated isobutylidene diurea with another fertilizer and/or with a secondary nutrient and/or with a trace element and/or with a plant protection agent and/or with a filler and/or with other fertilizer ingredients to form a mixed fertilizer.

Examples of other fertilizers include but are not limited to nitrogen fertilizers, phosphate fertilizers, alkaline fertilizers, potassium and/or magnesium containing fertilizers and/or manure and/or secondary nutrients and/or trace elements.

Examples of nitrogen fertilizers include organic fertilizer containing nitrogen, such as methylene urea, crotonylidene diurea, oxamide, melamine, substituted triazones, ethylene diurea, triuret and any mixtures of them.

For example, the other fertilizers may additionally contain urea or nitrogen, potassium, phosphorus and/or magnesium in the form of inorganic salts, or mixtures of them. Easily soluble nitrogen components are, for example, ammonium nitrate, ammonium sulfate, or urea. Other salts that may be used are, for example, MAP, DAP, potassium sulfate, potassium chloride, magnesium sulphate, calcium superphosphate, disodium hydrogen phosphate, ferric chloride, manganous chloride, calcium chloride, magnesium phosphate, ammonia and potassium oxide.

The other fertilizers can contain single-nutrient as well as multi-nutrient fertilizers as well as other possible fertilizer ingredients, for example, which contain nutrients such as nitrogen, potassium, or phosphorus, individually or, if necessary, in combination, in the form of their salts. Examples of these are NP, NK, PK, as well as NPK fertilizers such lime nitrate of ammonium, ammonia sulfate, ammonia sulfa-nitrate, or urea.

Examples of secondary nutrients include but are not limited to Ca, S, and B. Trace elements, for example selected from among Fe, Mn, Cu, Zn, Mo, or mixtures of them, may also be present for example in the form of inorganic salts. The amounts of secondary nutrients or trace elements in the mixed fertilizer may for example be chosen in the range from 0.5 to 5 wt.-%, based upon the total weight of the mixed fertilizer.

Examples of plant protection agents include but are not limited to insecticides, fungicides, growth regulators, nitrification inhibitors, and any mixtures of them.

Examples of fillers include but are not limited to clay, peat, etc.

Examples of other fertilizer ingredients are for example described in Ullmann's Encyclopedia of Industrial Chemistry, 5th edition, 1987, Volume A10, pages 363 to 401, DE-A-41 28 828, DE-A-19 05 834, or DE-A-196 31 764, which references are hereby incorporated by reference.

In another aspect, the invention relates to isobutylidene diurea obtained or obtainable by the process of the invention.

Preferably, the invention relates to isobutylidene diurea obtained or obtainable by the process of the invention, wherein the particle size of more than 80% of the isobutylidene diurea particles is in the range from 150 to 300 microns and wherein the size of the isobutylidene diurea does not exceed 500 microns.

In yet another aspect, the invention relates to mixed fertilizer obtainable by the process of the invention.

The isobutylidene diurea or the mixed fertilizer of the invention may also be coated in whole or in part, as for example described in EP-A-0 877 722 or DE-A-196 31 764, hereby incorporated by reference.

The isobutylidene diurea or the mixed fertilizer of the invention may for example be in the form of granules or a briquette, for example a briquette that is prepared by compression molding of granular isobutylidene diurea and a mineral oil.

In another aspect, the invention relates to the use of the isobutylidene diurea obtained in the process of the invention as a fertilizer or in feed.

The invention also relates to the use of the isobutylidene diurea obtainable by the process of the invention as a fertilizer or in feed.

The isobutylidene diurea obtained or obtainably by the process of the invention may be used—instead of urea—as a source of nitrogen in the nutrition of ruminants. Examples of ruminants include cattle, goats, sheep, giraffes, bison, moose, elk, yaks, water buffalo, deer, camels, alpacas, llamas, antelope, pronghorn, and nilgai.

The invention also relates to the use of the mixed fertilizer of the invention as a fertilizer.

The isobutylidene diurea or the mixed fertilizer of the invention may suitably be used for fertilization of horticultural or agricultural soils, for example lawns or ornamental plants. They may be applied to areas used for agriculture or horticulture according to generally known methods, see also Ullmann's Encyclopedia of Industrial Chemistry, 5th edition, 1987, Volume A10, pages 398 to 401, hereby incorporated by reference. They may be used for fertilizing methods in which the fertilizer is applied to the agricultural area more or less uniformly, but may also be used for targeted deposition in the vicinity of the plant root.

The isobutylidene diurea or the mixed fertilizer of the invention may be used in all sectors of plant cultivation, such as agriculture and horticulture, for example in fruit and vegetable cultivation.

Examples of plants which may be fertilized using the isobutylidene diurea or the mixed fertilizer of the invention include but are not limited to ornamental plants, lawns and cultures for consumption, such as apples, pears, strawberries, tomatoes, peppers, and others.

The isobutylidene diurea or the mixed fertilizer of the invention may be applied to the areas used for agriculture or horticulture according to usual methods, or mixed into the substrate of pot or container cultures, or sprinkled on.

For optimum promotion of growth of the plants, it is generally sufficient to apply the isobutylidene diurea or the mixed fertilizer of the invention to the agricultural surface once per growth period (preferably at its beginning).

In yet another aspect, the invention relates to a process comprising the step of applying the isobutylidene diurea or the mixed fertilizer of the invention to horticultural or agricultural soils.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term 'comprising' does not exclude the presence of other elements. It is therefore to be understood that a description on a process comprising certain steps also discloses a process consisting of these steps.

The invention will now be elucidated by way of the following examples without however being limited thereto.

EXAMPLES

Example 1 (Invention Example)

Condensation of isobutyraldehyde and urea using benzyltrimethyl ammonium chloride at 40° C.

The following quantities of reactants were taken in this experiment as described in Table 1.

TABLE 1

| (1) Isobutyraldehyde | 1.00 mole |
|---|---|
| (2) Urea | 2.00 mole |
| (3) Benzyltrimethyl ammonium chloride | 0.03 mole |
| (4) Water | 6.00 mole |

The condensation reaction carried out at 40° C. is described as follows: The reaction was performed in a 1.0 liter jacketed reactor equipped with a mechanical stirrer, thermocouple, condensor, and a dropping funnel. The temperature was measured using a K-type chromel-alumel thermocouple.

The reactants (isobutyraldehyde and urea) were taken in two reaction flask. To the urea flask was added measured quantity of water and stirred well to make aqueous urea solution.

The urea solution (52 wt % in demineralized water) was added to the reactor followed by requisite amount of benzyltrimethyl ammonium chloride. The reaction mixture was then stirred and heated up to 40° C. The liquid isobutyraldehyde was then added slowly through the dropping funnel at such a rate that temperature did not rise beyond 45° C. Slow addition of isobutyraldehyde is done to avoid significant exotherm. The rate of reaction was monitored by the disappearance of isobutyraldehyde using gas chromatography. The aliquot samples were taken out at every 2 minutes over a period of 20 minutes. The GC analysis showed ~100% conversion of isobutyraldehyde in the aliquot sample taken at 20 minutes. The product isobutylidine diurea formed as white solid was removed by filtration and phase-transfer catalyst stays in the aqueous layer. This reaction, including the scale-ups, is well reproducible.

The product isobutylidine diurea was then dried to a moisture content of <1.0%, and the yield of product obtained was >90%. The purity of the obtained isobutylidene diurea was ~96%. The Melting point of the product obtained is ~205° C. The elementary analysis of the $C_6H_{14}O_2N_4$ Calculated, C, 41.38%; H, 8.05%; 0, 18.39%; N, 32.18%. Analysed, C, 41.25%, H, 7.97%; 0, 18.31%; N, 32.14%.

Example II (Comparative Example)

Condensation of isobutyraldehyde and urea using sulfuric acid and phosphoric acid at 40° C.

The following quantities of reactants were taken in this experiment as described in Table 2.

TABLE 2

| (1) Isobutyraldehyde | 1.00 mole |
|---|---|
| (2) Urea | 2.00 mole |
| (3) Sulfuric Acid | 0.03 mole |
| (4) Phosphoric Acid | 0.03 mole |
| (5) Water | 6.00 mole |

The condensation reaction carried out at 40° C. is described as follows: The reaction was conducted in same manner as in U.S. Pat. No. 3,962,329.

The reactants (isobutyraldehyde and urea) were taken in two reaction flask. To the urea flask was added measured quantity of water and stirred well to make an aqueous urea solution.

The urea solution was added to the reactor followed by requisite amount of sulfuric acid and phosphoric acid. The mixture was then stirred and heated up to 40° C. The liquid isobutyraldehyde was then added slowly through the dropping funnel and no exotherm was observed and reaction was not initiated. The reaction was run at the same temperature for 30 minutes, but the white solid isobutylidene diurea product was not formed. The GC analysis did not show any significant conversion of isobutyraldehyde. Consequently, the unreacted isobutyraldehyde was ~100%.

Example III (Comparative Example)

Condensation of isobutyraldehyde and urea using ammonium sulfate at 40° C.

The following quantities of reactants were taken in this experiment as described in Table 3.

TABLE 3

| (1) Isobutyraldehyde | 1.00 mole |
|---|---|
| (2) Urea | 2.00 mole |
| (3) Ammonium Sulfate | 0.03 mole |
| (4) Water | 6.00 mole |

The condensation reaction carried out at 40° C. is described as follows: The reaction was conducted in same manner as in U.S. Pat. No. 4,062,890 except that ammonium sulfate alone was used as a catalyst and the collagen-derived protein was absent.

The reactants (isobutyraldehyde and urea) were taken in two reaction flask. To the urea flask was added measured quantity of water and stirred well to make aqueous urea solution.

The urea solution was added to the reactor followed by requisite amount of ammonium sulfate. The reaction mixture was then stirred and heated up to 40° C. The liquid isobutyraldehyde was then added slowly through the dropping funnel and no exotherm was observed and reaction was not initiated. The reaction was run at the same temperature for 30 minutes, but the white solid isobutylidene diurea product was not formed. Consequently, the unreacted isobutyraldehyde was ~100%.

CONCLUSION

The examples presented herein show that the process of the present invention can be performed at a low temperature, whereas the processes of U.S. Pat. No. 3,962,329 and U.S. Pat. No. 4,062,890 cannot. Therewith, the process of the invention provides a process for the preparation of IBDU, which process of the invention is easy to handle (e.g. no need for special metallurgy or handling techniques) and which can be performed at an acceptable rate at a low temperature and which additionally gives IBDU at a high yield and with a high purity.

Set forth below are some embodiments of the process of forming isobutylidene diurea, the isobutylidene diurea formed therefrom, and uses thereof.

Embodiment 1

A process for forming isobutylidene diurea, comprising: reacting isobutyraldehyde with an aqueous solution of urea in the presence of a phase transfer catalyst to form isobutylidene diurea.

Embodiment 2

The process according to Embodiment 1, wherein the reacting of the isobutyraldehyde with the aqueous solution of urea in the presence of the phase transfer catalyst is performed in one pot.

Embodiment 3

The process according to Embodiment 1 or Embodiment 2, wherein the phase transfer catalyst is a quaternary ammonium salt.

Embodiment 4

The process according to any one of Embodiments 1-3, wherein the phase transfer catalyst is benzyltriethylammonium chloride.

Embodiment 5

The process according to any one of Embodiments 1-4, wherein the amount of phase transfer catalyst is 0.5 to 5 mol % of the isobutyraldehyde.

Embodiment 6

The process according to any one of Embodiments 1-5, wherein the amount of phase transfer catalyst is 1 to 5 mol % of the isobutyraldehyde.

Embodiment 7

The process according to any one of Embodiments 1-6, wherein the amount of phase transfer catalyst is 2 to 4 mol % of the isobutyraldehyde.

Embodiment 8

The process according to any one of Embodiments 1-7, wherein the amount of phase transfer catalyst is about 3 mol % of the isobutyraldehyde.

Embodiment 9

The process according to any one of Embodiments 1-8, wherein the aqueous solution of the urea contains the urea in an amount of 50 to 85 wt %.

Embodiment 10

The process according to any one of Embodiments 1-9, further comprising isolating the isobutyilidene diurea to obtain isolated isobutylidene diurea.

Embodiment 11

The process according to any one of Embodiments 1-10, further comprising mixing the formed isobutylidene diurea or the isolated isobutylidene diurea with another fertilizer and/or with a secondary nutrient and/or with a trace element and/or with a plant protection agent and/or with a filler and/or with other fertilizer ingredients to form a mixed fertilizer.

Embodiment 12

The process according to any one of Embodiments 1-10, further comprising mixing the formed isobutylidene diurea or the isolated isobutylidene diurea with at least one of another fertilizer, a secondary nutrient, a trace element, a plant protection agent, a filler, other fertilizer ingredients, and combinations comprising at least one of the foregoing, to form a mixed fertilizer.

Embodiment 13

A mixed fertilizer obtainable by the process of any of Embodiments 11-12.

Embodiment 14

The use of the mixed fertilizer of Embodiment 13 as a fertilizer.

Embodiment 15

The isobutylidene diurea obtainable from by the process according to any one of Embodiments 1-10.

Embodiment 16

The isobutylidene diurea according to Embodiment 15, wherein a particle size of more than 80 wt % of the isobutylidene diurea particles is 150 to 300 micrometers.

Embodiment 17

The isobutylidene diurea according to any of Embodiments 15-16, wherein the size of the isobutylidene diurea does not exceed 500 micrometers.

Embodiment 18

The use of the isobutylidene diurea according to any of Embodiments 15-17 as a fertilizer or in feed.

Embodiment 19

The process, comprising: applying the isobutylidene diurea of any of Embodiments 15-18 or the mixed fertilizer of Embodiment 13 to horticultural or agricultural soils.

The invention claimed is:

1. A process for forming isobutylidene diurea, comprising:
reacting isobutyraldehyde with an aqueous solution of urea in the presence of a phase transfer catalyst to form isobutylidene diurea, wherein the phase transfer catalyst is a quaternary ammonium salt.

2. The process according to claim 1, wherein the reacting of the isobutyraldehyde with the aqueous solution of urea in the presence of the phase transfer catalyst is performed in one pot.

3. The process according to claim 1, wherein the phase transfer catalyst is benzyltriethylammonium chloride.

4. The process according to claim 1, wherein the amount of phase transfer catalyst is 0.5 to 5 mol % of the isobutyraldehyde.

5. The process according to claim 1, wherein the amount of phase transfer catalyst is 1 to 5 mol % of the isobutyraldehyde.

6. The process according to claim 1, wherein the amount of phase transfer catalyst is 2 to 4 mol % of the isobutyraldehyde.

7. The process according to claim 1, wherein the aqueous solution of the urea contains the urea in an amount of 50 to 85 wt %.

8. The process according to claim 1, further comprising isolating the isobutyilidene diurea to obtain isolated isobutylidene diurea.

9. The process according to claim 1, further comprising mixing the formed isobutylidene diurea or the isolated isobutylidene diurea with another fertilizer and/or with a secondary nutrient and/or with a trace element and/or with a plant protection agent and/or with a filler and/or with other fertilizer ingredients to form a mixed fertilizer.

* * * * *